United States Patent
Matsuo

(10) Patent No.: US 11,865,292 B2
(45) Date of Patent: Jan. 9, 2024

(54) TUBE CONNECTOR, EXTRACORPOREAL CIRCULATION CIRCUIT, AND BLOOD PURIFICATION DEVICE

(71) Applicant: NIKKISO CO., LTD., Tokyo (JP)

(72) Inventor: Sumiaki Matsuo, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 455 days.

(21) Appl. No.: 17/284,079

(22) PCT Filed: Aug. 1, 2019

(86) PCT No.: PCT/JP2019/030211
§ 371 (c)(1),
(2) Date: Apr. 9, 2021

(87) PCT Pub. No.: WO2020/084855
PCT Pub. Date: Apr. 30, 2020

(65) Prior Publication Data
US 2021/0346669 A1    Nov. 11, 2021

(30) Foreign Application Priority Data
Oct. 22, 2018    (JP) .................................. 2018-198587

(51) Int. Cl.
*A61M 39/10* (2006.01)
*A61M 1/26* (2006.01)
(Continued)

(52) U.S. Cl.
CPC ............ *A61M 39/10* (2013.01); *A61M 1/267* (2014.02); *A61M 60/113* (2021.01);
(Continued)

(58) Field of Classification Search
CPC .... A61M 39/10; A61M 1/267; A61M 60/113; A61M 60/279; A61M 60/37;
(Continued)

(56) References Cited

U.S. PATENT DOCUMENTS

2007/0129705 A1    6/2007    Trombley, III et al.
2015/0265756 A1    9/2015    Yokomizo

FOREIGN PATENT DOCUMENTS

JP    3007076 U    11/1994
JP    3007076 U    2/1995
(Continued)

OTHER PUBLICATIONS

Translation of International Preliminary Report on Patentability and Written Opinion Search Report dated May 6, 2021 issued in PCT/JP2019/030211.
(Continued)

*Primary Examiner* — Terry K Cecil
(74) *Attorney, Agent, or Firm* — Scully, Scott, Murphy & Presser, PC

(57) ABSTRACT

A tube connector is configured to connect between a main tube and a peristaltically-actuated tube. The tube connector includes a first connection part configured to be connected to the main tube; a second connection part configured to be connected to the peristaltically-actuated tube; a communication part being provided between the first connection part and the second connection part and having a communication flow path for communicating between a first flow path through which fluid flows in the first connection part and a second flow path through which the fluid flows in the second connection part; and a main body section. The first flow path and the second flow path are formed to have a constant diameter and are formed so as to extend along the axial direction of the main body section. A diameter of the first flow path is smaller than a diameter of the second flow path. The communication flow path is formed so as to gradually enlarge in diameter from a first flow path side to a second flow path side. A central axis of the first flow path and a (Continued)

central axis of the second flow path are shifted toward the radial direction of the main body section.

8 Claims, 8 Drawing Sheets

(51) Int. Cl.
  *A61M 60/113* (2021.01)
  *A61M 60/37* (2021.01)
  *A61M 60/279* (2021.01)
  *A61M 1/36* (2006.01)
  *A61M 60/109* (2021.01)
(52) U.S. Cl.
  CPC .......... *A61M 60/279* (2021.01); *A61M 60/37* (2021.01); *A61M 1/3627* (2013.01); *A61M 1/3644* (2014.02); *A61M 60/109* (2021.01)
(58) Field of Classification Search
  CPC .............. A61M 1/3627; A61M 1/3644; A61M 60/109; A61M 60/835; A61M 5/36; A61M 5/14228; A61M 60/845; A61M 1/3643; A61M 2039/0009; A61M 2206/10; A61M 1/367
  See application file for complete search history.

(56) References Cited

FOREIGN PATENT DOCUMENTS

| | | |
|---|---|---|
| JP | 2011-212174 A | 10/2011 |
| JP | 2014-008376 A | 1/2014 |
| WO | 2014017604 A1 | 1/2014 |

OTHER PUBLICATIONS

International Search Report dated Oct. 15, 2019 issued in PCT/JP2019/030211.
Extended European Search Report dated Jun. 24, 2022 from related EP 19 875 879.9.

TUBE CONNECTOR, EXTRACORPOREAL CIRCULATION CIRCUIT, AND BLOOD PURIFICATION DEVICE

TECHNICAL FIELD

The present invention relates to a tube connector, an extracorporeal circulation circuit, and a blood purification device.

BACKGROUND ART

In a blood purification system used for hemodialysis, a blood pump comprising an electric peristaltic pump (squeeze pump) has been used. A tube connector is used for connecting a peristaltically-actuated tube used for the blood pump and a main tube used in an extracorporeal circulation circuit.

In the tube connector described in Patent Document 1, the diameter of a first flow path is larger than that of a second flow path, and a communication flow path is formed in such a manner as to gradually increase in diameter from the first flow path-side to the second flow path-side. The first flow path and the second flow path are formed coaxially (in such a manner that the center axes of both the first and second flow paths coincide with each other).

CITATION LIST

Patent Literature

Patent Document 1: JP2011-212174A

SUMMARY OF INVENTION

Technical Problem

At the time of hemodialysis, first, a work called "priming" for filling a priming liquid such as a physiological saline solution into a blood circuit is performed. In the conventional tube connector, when an axial direction thereof is arranged along a substantially horizontal direction, bubbles tend to stay in the tube connector at this time of priming. Therefore, the operator must perform the work for removing the bubbles, so that the workability is deteriorated, and it becomes difficult to automate the priming.

In addition, there is a problem in that since the upstream side of the blood pump becomes negative at the time of operation of the blood pump, the dissolved gas in the blood becomes bubbles to be retained in the tube connector.

In Patent Document 1, the communication flow path is formed in a tapered shape, and a spread angle thereof is reduced to suppress the retention of the bubbles. In this structure, however, when the difference between the diameters of the first flow path and the second flow path is large, a communication part becomes very long, so that the tube connector can be enlarged in size.

Accordingly, the object of the present invention is to provide a tube connector, an extracorporeal circulation circuit, and a blood purification device that are compact and can suppress the retention of the bubbles

Solution to Problem

According to one aspect of the present invention, a tube connector is configured to connect between a main tube comprising a flexible tubular member and a peristaltically-actuated tube comprising a flexible tubular member and being configured to be squeezed in a longitudinal direction while being compressed in a radial direction by a squeezing part to make an internal liquid flow therethrough, the tube connector comprises: a first connection part configured to be connected to the main tube; a second connection part configured to be connected to the peristaltically-actuated tube; a communication part being provided between the first connection part and the second connection part and having a communication flow path for communicating between a first flow path through which fluid flows in the first connection part and a second flow path through which the fluid flows in the second connection part; and a main body section being constituted by sequentially providing the first connection part, the communication part, and the second connection part in an axial direction of the main body section, wherein the first flow path and the second flow path are formed to have a constant diameter and are formed so as to extend along the axial direction of the main body section, wherein a diameter of the first flow path is smaller than a diameter of the second flow path, wherein the communication flow path is formed so as to gradually enlarge in diameter from a first flow path side to a second flow path side, and wherein a central axis of the first flow path and a central axis of the second flow path are shifted toward the radial direction of the main body section.

According to another aspect of the present invention, an extracorporeal circulation circuit, comprises a main tube for extracorporeal circulation of a blood of a patient; a blood purifier inserted in a middle of the main tube; a blood pump comprising a peristaltic type pump inserted in the middle of the main tube and including a peristaltically-actuated tube comprising a flexible tubular member and being configured to be squeezed in a longitudinal direction while being compressed in a radial direction by a squeezing part to make an internal liquid flow therethrough; and a pair of tube connectors configured to connect both ends of the peristaltically-actuated tube to the main tube, wherein at least the tube connector provided on an upstream side in blood flow is the tube connector according to the present invention.

According to still another aspect of the present invention, a blood purification device, comprising the extracorporeal circulation circuit according to present invention; and a dialysate supply circuit for supplying dialysate to the blood purifier.

Advantageous Effect of Invention

According to one aspect of the present invention, it is possible to provide a small-sized tube connector, an extracorporeal circulation circuit, and a blood purification device that are capable of suppressing the retention of bubbles.

BRIEF DESCRIPTION OF DRAWINGS

FIG. 5B is a side view showing an enlarged part.

DESCRIPTION OF EMBODIMENTS

Embodiments

Next, embodiments of the present invention will be described below with reference to the accompanying drawings.

(Description of Extracorporeal Circulation Circuit)

Figure 1:
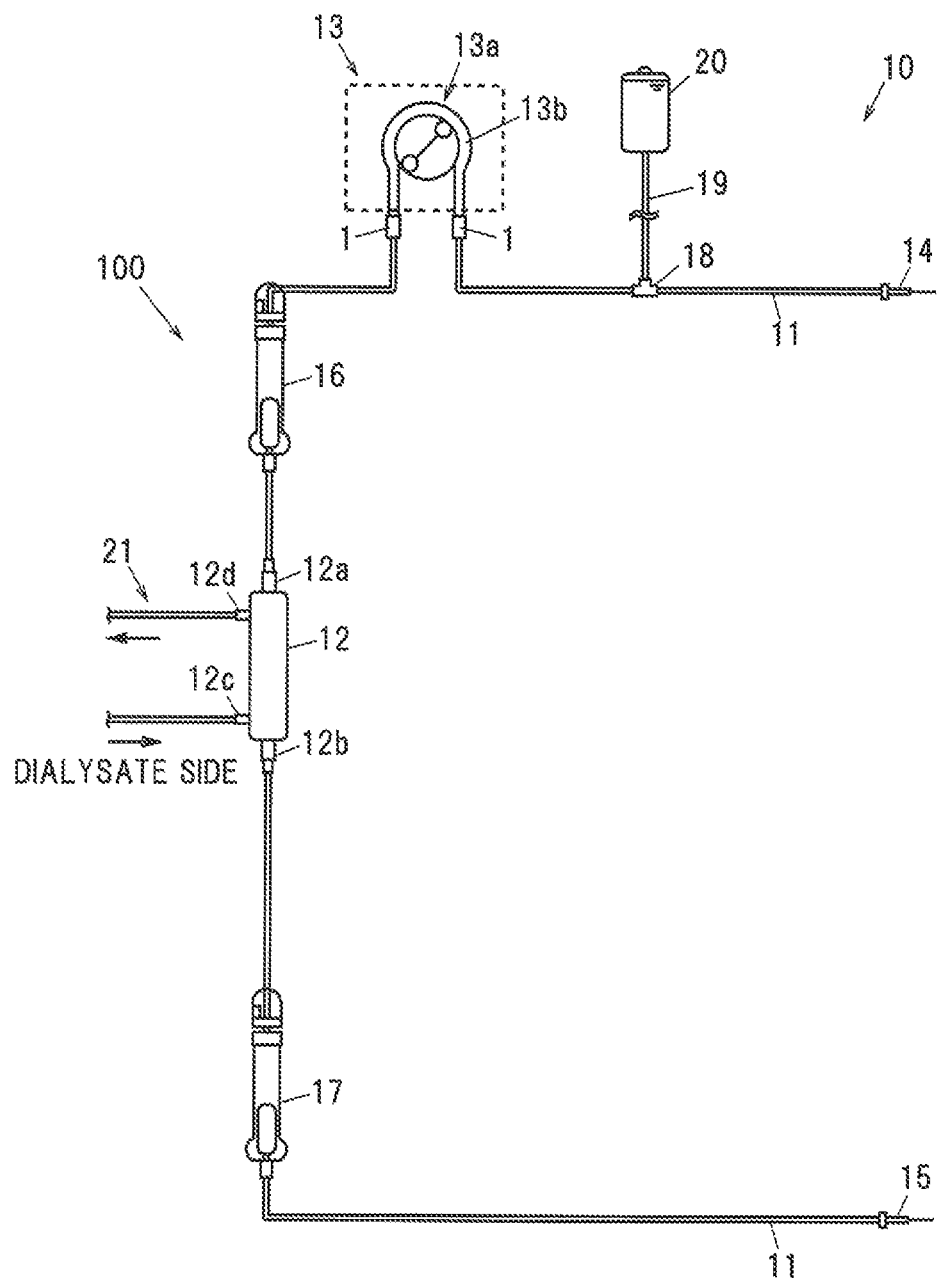
FIG. 1 is a schematic block diagram showing an extracorporeal circulation circuit according to an embodiment of the present invention.

FIG. 1 is a schematic block diagram showing an extracorporeal circulation circuit according to the present embodiment. As shown in FIG. 1, an extracorporeal circulation circuit 10 is provided with a main tube 11 for extracorporeal circulation of the patient's blood, a blood purifier 12 inserted in the middle of the main tube 11, and a blood pump 13.

The main tube 11 is composed of a flexible tubular member. An artery side puncture needle 14 can be attached to one end of the main tube 11. A vein side puncture needle 15 can be attached to the other end of the main tube 11

In the main tube 11 provided between the artery side puncture needle 14 and the vein side puncture needle 15, the blood pump 13, an artery side air trap chamber 16, a blood purifier 12, and a vein side air trap chamber 17 are successively provided from one end side to the other end side. During hemodialysis, the patient's blood is introduced into the main tube 11 from the artery side puncture needle 14 and returned to the patient from the vein side puncture needle 15

A T-shaped tube 18 is inserted into the main tube 11 between the artery side puncture needle 14 and the blood pump 13, and a priming liquid supply line 19 for supplying a priming liquid such as a physiological saline solution is connected via the T-shaped tube 18. The priming liquid supply line 19 is composed of a flexible tube-like member, and a storage bag 20 for storing the priming liquid is connected to an end part opposite to the T-shaped tube 18. Thus, the priming liquid stored in the storage bag 20 can be supplied into the main tube 11 through the priming liquid supply line 19 and the T-shaped tube 18. The priming liquid supply line 19 can optionally be opened and closed by a flow path closing mechanism (not shown).

The blood pump 13 is composed of an electric peristaltic type pump, and has a peristaltically-actuated tube 13b which is configured to be squeezed in a longitudinal direction while being compressed in a radial direction by a squeezing part 13a, thereby make an internal liquid flow therethrough. The peristaltically-actuated tube 13b is made of a flexible tubular member, and the outer diameter and inner diameter thereof are larger than those of the main tube 11. The outer diameter of the peristaltically-actuated tube 13b is, e.g., 12 mm, and the outer diameter of the main tube 11 is, e.g., 6 mm. Both ends of the peristaltically-actuated tube 13b are connected to the main tube 11 through the tube connector 1 according to the present embodiment. Details of the tube connector 1 are described later.

The artery side air trap chamber 16 is provided for removing the bubbles from the blood discharged from the blood pump 13. Similarly, the vein side air trap chamber 17 is used for removing the bubbles from the blood after passing through the blood purifier 12.

The blood purifier 12 is also called as "dialyzer", and accommodates a plurality of hollow fibers having micropores formed therein in a housing, and a blood inlet port 12a, a blood outlet port 12b, a dialysate inlet port 12c, and a dialysate outlet port 12d are respectively provided in the housing. A main tube 11 on the side of an artery side puncture needle 14 is connected to the blood inlet port 12a, and a main tube 11 on the side of a vein side puncture needle 15 is connected to the blood outlet port 12b. The dialysate inlet port 12c and the dialysate outlet port 12d are connected to a dialysate supply circuit 21 that supplies dialysate. A blood purification device 100 is provided with the dialysate supply circuit 21 and the extracorporeal circulation circuit 10 according to the present embodiment.

The patient's blood introduced into the blood purifier 12 passes through the hollow fibers within the blood purifier 12. The dialysate introduced into the blood purifier 12 passes through the outside of the hollow fibers. Thus, the waste or the like in the blood is transmitted to the dialysate side through the hollow fibers, and the blood can be purified. The cleaned blood is defoamed by the vein side air trap chamber 17, and then returned to the body of the patient via the vein side puncture needle 15.

(Description of Tube Connector 1)

Figure 2A:
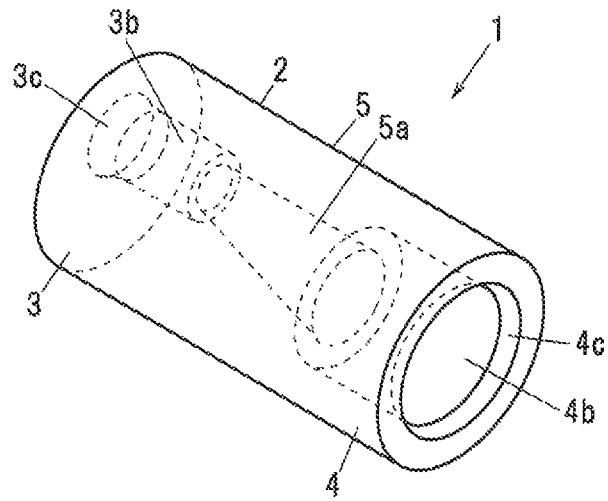
FIG. 2A is a perspective view of a tube connector.
Figure 2B:
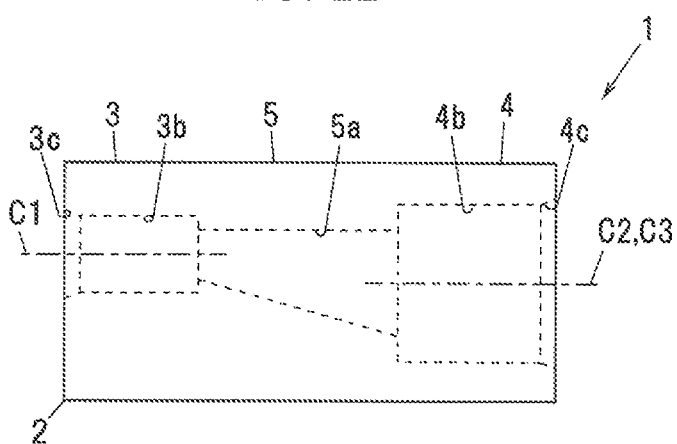
FIG. 2B is a side view of a tube connector.
Figure 2C:
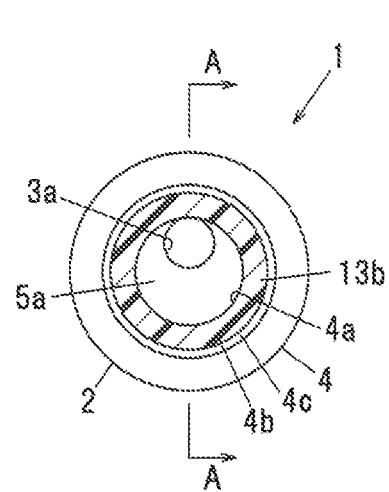
FIG. 2C is a cross-sectional view of the tube connector viewed from a connection side of a peristaltically-actuated tube when a main tube and the peristaltically-actuated tube are connected.
Figure 2D:
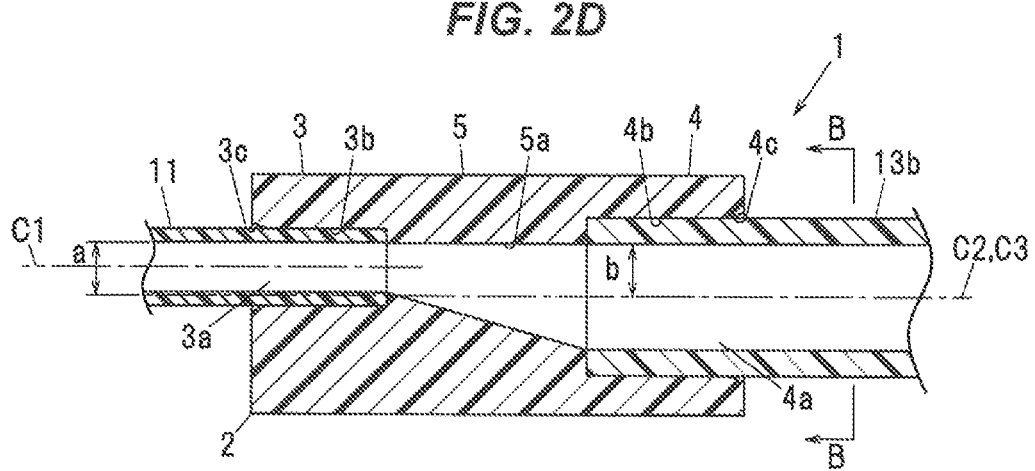
FIG. 2D is a cross-sectional view taken along line A-A of FIG. 2C.

FIG. 2A is a perspective view of the tube connector 1 used in the extracorporeal circulation circuit 10 of FIG. 1, FIG. 2B is a side view of the tube connector 1, FIG. 2C is a cross-sectional view viewed from the connection side of the peristaltically-actuated tube 13b when the main tube 11 and the peristaltically-actuated tube 13b are connected, and FIG. 2D is a cross-sectional view taken along line A-A of FIG. 2C. It should be noted that FIG. 2C is a cross-sectional view taken along line B-B in FIG. 2D.

As shown in FIGS. 2A to 2D, the tube connector 1 is a resin molded component and is a member for connecting the main tube 11 and the peristaltically-actuated tube 13b. The tube connector 1 has a main body 2 formed in a cylindrical shape as a whole.

The tube connector 1 is provided with a first connection part 3 configured to be connected to the main tube 11, a second connection part 4 configured to be connected to the peristaltically-actuated tube 13b, and a communication part 5 provided between the first connection part 3 and the second connection part 4 and having a communication flow path 5a for communicating between a first flow path 3a through which fluid flows in the first connection part 3 and a second flow path 4a through which the fluid flows in the second connection part 4. The main body 2 is constituted by sequentially providing the first connection part 3, the communication part 5, and the second connection part 4 in the axial direction.

The first flow path 3a and the second flow path 4a are formed to have a substantially constant diameter and are formed so as to extend along the axial direction of the main body 2. The diameter of the first flow path 3a is smaller than the diameter of the second flow path 4a. In this embodiment, the first connection part 3 has a first insertion hole 3b for inserting an end part of the main tube 11 thereinto, and a hollow part of the main tube 11 inserted into the first insertion hole 3b serves as the first flow path 3a. Similarly, the second connection part 4 has a second insertion hole 4b for inserting an end part of the peristaltically-actuated tube 13b thereinto, and a hollow part of the peristaltically-actuated tube 13b inserted into the second insertion hole 4b serves as the second flow path 4a. In this embodiment, in order to facilitate the insertion of the main tube 11 into the first insertion hole 3b, a tapered part 3c which is enlarged toward an opening side is formed at an end part on the opening side of the first insertion hole 3b. Similarly, in order to facilitate the insertion of the peristaltically-actuated tube 13b into the second insertion hole 4b, a tapered part 4c which is enlarged toward an opening side is formed at an end part on the opening side of the second insertion hole 4b.

Figure 3:
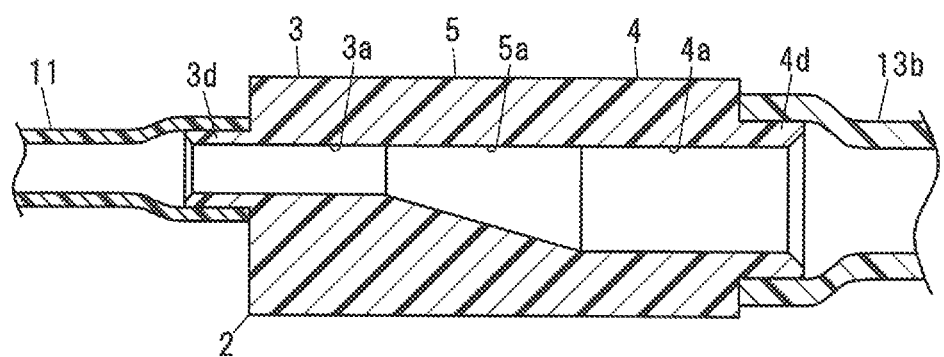
FIG. 3 is a cross-sectional view showing a modification example of the tube connector.

It should be noted that the present invention is not limited thereto. As shown in FIG. 3, for example, the tube connector 1 may be configured in such a manner that connection projections 3d and 4d are provided so as to project outward in the axial direction at the first connection part 3 and the second connection part 4, and the connection projections 3d, 4d are inserted into the main tube 11 or the peristaltically-actuated tube 13b. However, in this case, the flow in the vicinity of tip parts of the connection projections 3d and 4d is likely to be stagnant, and it is considered to cause the stagnation of the bubbles. Therefore, it is more desirable to insert the ends of the main tube 11 and the peristaltically-actuated tube 13b into the insertion holes 3b, 4b, as in the present embodiment, from the viewpoint of suppressing the retention of the bubbles.

Returning to FIGS. 2A to 2D, the communication flow path 5a is connected to the first flow path 3a and the second flow path 4a substantially without level difference (step). That is, in this embodiment, the communication flow path 5a is connected to the hollow part of the main tube 11 inserted into the first insertion hole 3b and the hollow part of the peristaltically-actuated tube 13b inserted into the second insertion hole 4b substantially without level difference. However, a slight level difference caused by manufacturing tolerance or the like may be present between the communication flow path 5a and the first flow path 3a and the second flow path 4a. Since the increase in the level difference may cause the stagnation of the flow of the fluid (blood or priming liquid) and the retention of bubbles tends to occur, it is desirable to minimize the level difference as much as possible.

The communication flow path 5a is formed so as to gradually enlarge in diameter from the first flow path 3a side to the second flow path 4a side. In this embodiment, the communication flow path 5a is formed in a tapered shape gradually enlarged in diameter from the first flow path 3a side to the second flow path 4a side, but the present invention is not limited thereto, and, for example, a part of the inner peripheral surface may be rounded (curved) in a side view. When there is a level difference in the communication flow path 5a, since the bubbles are retained in the level difference, the communication flow path 5a is formed into a smooth shape having no level difference.

Here, the reason why the retention of bubbles occurs in the tube connector 1 is examined. In a conventional tube connector in which the first flow path 3a and the second flow path 4a are coaxially formed, when a taper angle (spread angle) of the communication flow path 5a is increased, especially when the fluid flows from the first flow path 3a side to the second flow path 4a side, the flow tends to stagnate near the end part on the communication part 5 side of the second flow path 4a, and the retention of the bubbles occurs. The retained bubbles are accumulated in an upper side in the vertical direction in the use state.

Therefore, the inventors contemplated to make the bubbles accumulated in the upper side in the vertical direction flow to the downstream side by the force of the fluid flowing from the first flow path 3a side. In order to increase the force of the fluid upward in the vertical direction, the first flow path 3a may be formed by shifting the first flow path 3a upward in the vertical direction.

That is, in the tube connector 1 according to the present embodiment, a central axis C1 of the first flow path 3a and a central axis C2 of the second flow path 4a are shifted toward the radial direction of the main body 2. When using the tube connector 1, the tube connector 1 is arranged in such a manner that the central axis C1 of the first flow path 3a is shifted upward in the vertical direction in the use state with respect to the central axis C2 of the second flow path 4a.

In order to further suppress the retention of the bubbles, it is preferable that the upper part of the first flow path 3a in the vertical direction and the upper part of the second flow path 4a in the vertical direction are aligned, or alternatively, the first flow path 3a is formed above the second flow path 4a in the vertical direction. That is, a part of the inner peripheral surface of the first flow path 3a and a part of the inner peripheral surface of the second flow path 4a are formed at positions corresponding to each other in the radial direction of the main body 2, or a part of the first flow path 3a may be disposed outside the second flow path 4a in the radial direction of the main body 2. In other words, it is preferable that a maximum distance a along the radial direction of the main body 2 from the central axis C3 of the main body 2 to the inner peripheral surface of the first flow path 3a is equal to or more than a maximum distance b along the radial direction of the main body 2 from the central axis C3 of the main body 2 to the inner peripheral surface of the second flow path 4a.

However, in the case where the distance a is larger than the distance b, that is, in the case where the first flow path 3a is formed above the second flow path 4a in the vertical direction, when the fluid flows from the second flow path 4a side to the first flow path 3a side, the bubbles may tend to stagnate in the end part on the communication part 5 side of the first flow path 3a. Thus, it is most desirable that the distance a and the distance b coincide with each other, that is, the upper part of the first flow path 3a in the vertical direction and the upper part of the second flow path 4a in the vertical direction are aligned (i.e., the part of the inner peripheral surface of the first flow path 3a and the part of the inner peripheral surface of the second flow path 4a are formed at positions corresponding to each other in the radial direction of the main body 2). As a result, a common tube connector 1 can be used on the upstream side and the downstream side of the peristaltically-actuated tube 13b, thereby contributing to the reduction of the number of components and the cost reduction. In this case, as shown in FIG. 2C, when viewed from the connection side of the peristaltically-actuated tube 13b, the inner peripheral surface of the first flow path 3a is brought into contact with the inner peripheral surface of the second flow path 4a. In this embodiment, the central axis C3 of the main body 2 coincides with the central axis C2 of the second flow path 4a, but the central axis C3 of the main body 2 and the central axis C2 of the second flow path 4a may be shifted toward the radial direction of the main body 2.

Figure 4A:
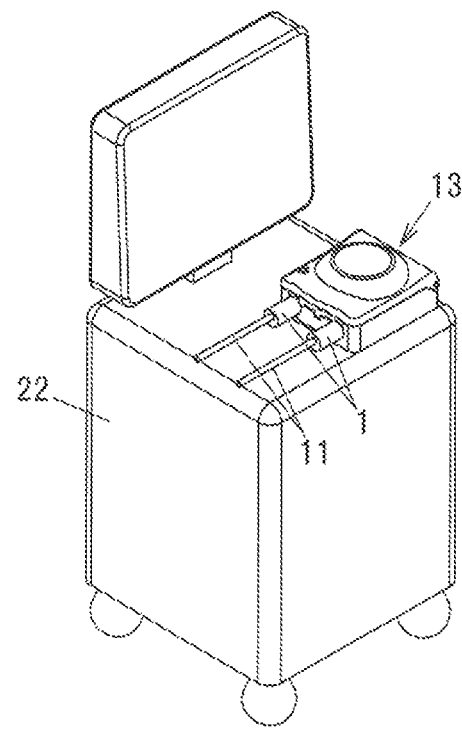
FIG. 4A is a perspective view showing an example of the arrangement of a blood pump and a direction of the tube connector.
Figure 4B:
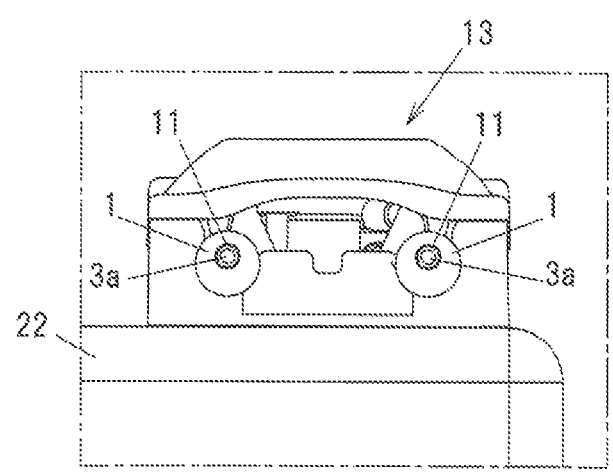
FIG. 4B is an enlarged side view showing an essential part in an example of the arrangement of the blood pump and the direction of the tube connector.

Next, the installation orientation of the blood pump 13 and the direction of the tube connector 1 are examined. As shown in FIG. 4A, when the blood pump 13 is placed on an upper surface of the base 22, the main tubes 11 on the inlet side and the outlet side, which are extended from the blood pump 13, are arranged side by side in the horizontal direction. In such a case, as shown in FIG. 4B, the tube connector 1 is arranged in such a manner that the first flow path 3a (central axis C1) is shifted in a direction perpendicular to an arrangement direction of the main tube 11 with respect to the second flow path 4a (central axis C2)

Figure 5A:
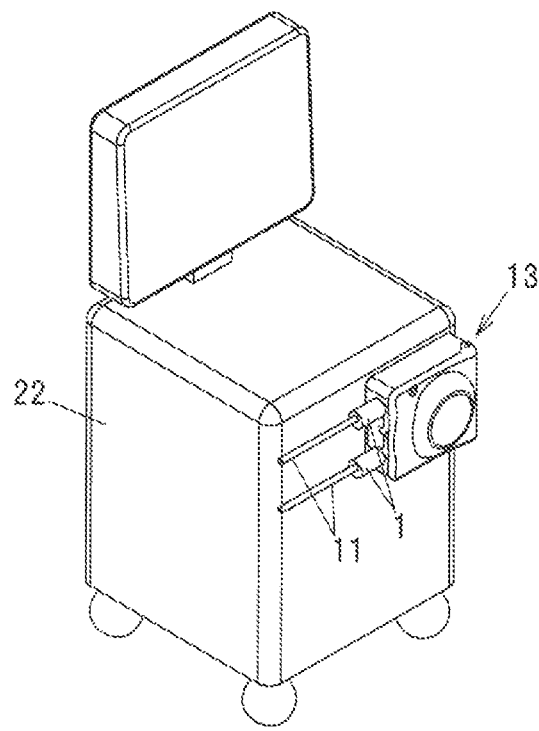
FIG. 5A is a perspective view showing an example of the arrangement of the blood pump and the direction of the tube connector.
Figure 5B:
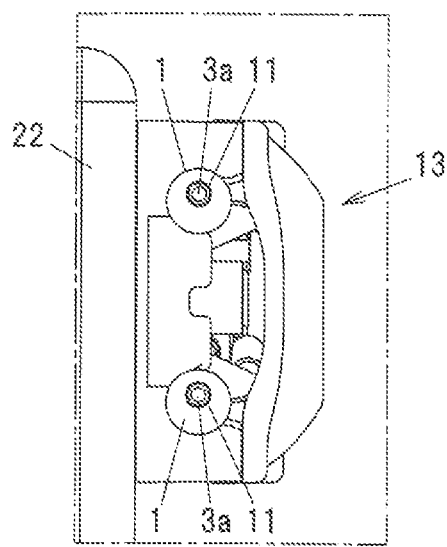
FIG. 5B is an enlarged side view showing an essential part in an example of the arrangement of the blood pump and the direction of the tube connector.

Also, as shown in FIG. 5A, when the blood pump 13 is attached to a side surface of the base 22, the main tubes 11 on the inlet side and the outlet side, which are extended from the blood pump 13, are arranged side by side in the vertical direction. In this case, as shown in FIG. 5B, the tube connector 1 is arranged in such a manner that the first flow path 3a (central axis C1) is shifted in a direction parallel to the arrangement direction of the main tube 11 with respect to the second flow path 4a (central axis C2). The blood pump 13 may be arranged obliquely, such as when the blood pump 13 is placed on the inclined base 22. In this case, it is preferable to adjust the arrangement direction of the tube connector 1 as necessity in such a manner that the first flow path 3a (central axis C1) is shifted vertically upward relative to the second flow path 4a (central axis C2).

Figure 6A:
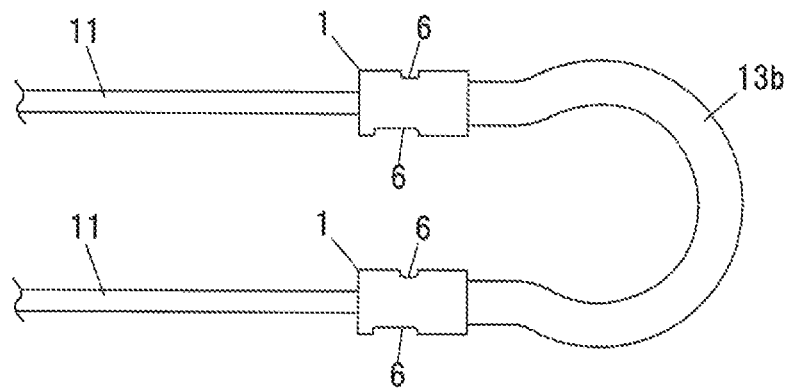
FIG. 6A is a diagram illustrating an example of a mounting direction regulating means.
Figure 6B:
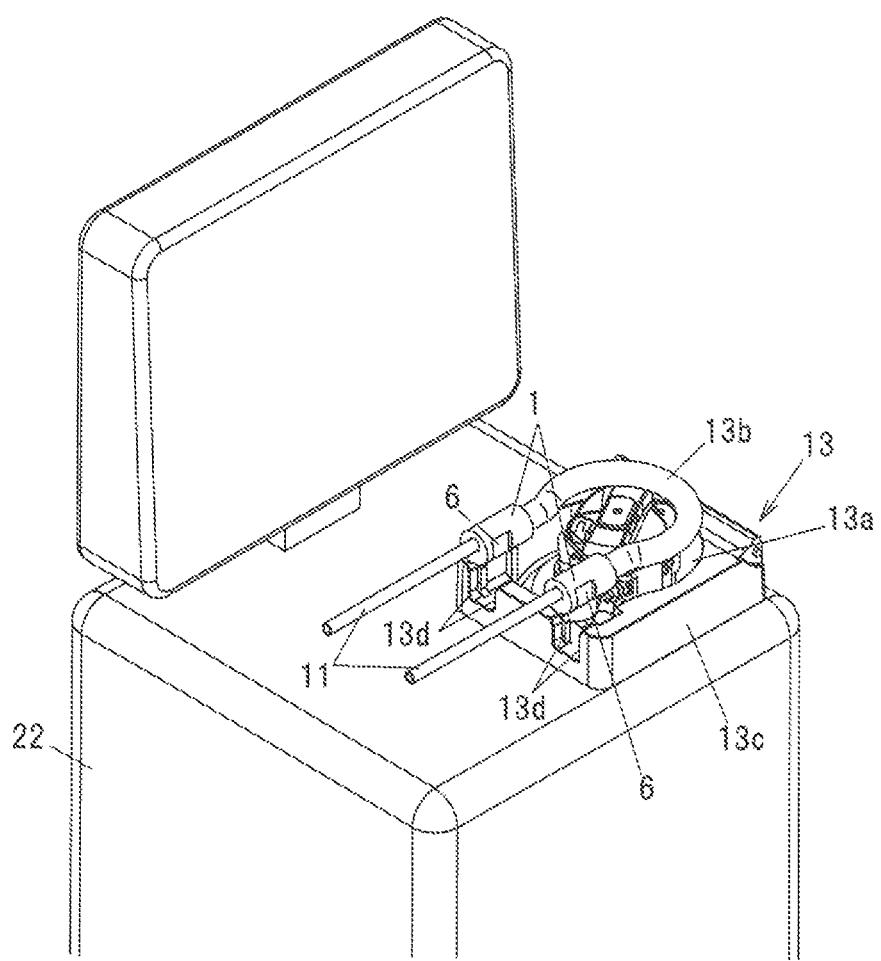
FIG. 6B is a diagram illustrating an example of the mounting direction regulating means.

The extracorporeal circulation circuit 10 may have a mounting direction regulation means for regulating a mounting direction of the tube connector 1 in such a manner that the central axis C1 of the first flow path 3a is shifted upward in the vertical direction in the use state with respect to the central axis C2 of the second flow path 4a. Specific configurations of the mounting direction regulating means are not particularly limited. For example, as shown in FIG. 6A, grooves 6 having different widths may be provided on both sides of the tube connector 1, and, as shown in FIG. 6B, guide projections 13d having different widths to be inserted into both the grooves 6 may be provided in a case 13c of the blood pump 13, so that the mounting direction of the tube connector 1 can be regulated. For example, when the peristaltically-actuated tube 13b is set to the blood pump 13, it may be difficult to attach the tube connector 1 in a desired direction due to twisting of the peristaltically-actuated tube 13b, but by providing the mounting direction regulating means, the adverse effect of twisting or the like of the peristaltically-actuated tube 13b is suppressed, and the tube connector 1 can be easily attached in the desired direction.

Figure 7:
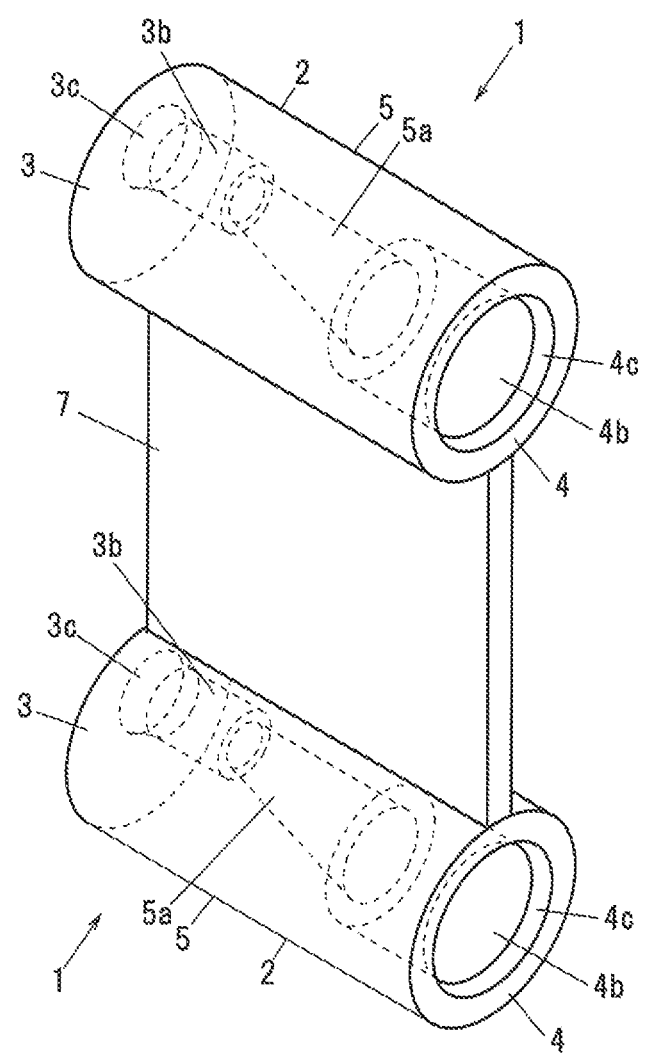
FIG. 7 is a perspective view of a case where a pair of tube connectors are integrated.

As shown in FIG. 7, the tube connector 1 connected to the upstream side of the peristaltically-actuated tube 13b and the tube connector 1 connected to the downstream side of the peristaltically-actuated tube 13b may be integrally constituted as one piece. Although a pair of tube connectors 1 are connected by a plate-like connecting piece 7 in this case, the present invention is not limited thereto. A pair of tube connectors 1 may be connected by a columnar or rod-like connecting piece, for example, and the tube connector 1 may be connected by a fixing member provided separately from the tube connector 1. By integrating a pair of tube connectors 1, both the tube connectors 1 can be attached by one fitting operation, and workability is improved.

(Operation and Effect of Embodiments)

As described above, in the tube connector 1 according to the present embodiment, the central axis C1 of the first flow path 3a and the central axis C2 of the second flow path 4a are shifted toward the radial direction of the main body 2. As a result, the tube connector 1 is arranged in such a manner that the first flow path 3a is shifted upward in the vertical direction with respect to the second flow path 4a, thereby facilitating the flow of the bubbles to the downstream side by the force of the fluid flowing from the first flow path 3a. As a result, bubble removal work at the time of priming becomes unnecessary, and the priming can be automated.

Further, even when the dissolved gas in the blood becomes bubbles, the bubbles are easily made to flow to the downstream side. In recent years, it is required to automate the blood return operation after the completion of hemodialysis in order to save labor of operation during hemodialysis. Since the blood pump 13 is reversely rotated and the blood flows in the reverse direction during the blood return operation, if the bubbles are accumulated in the tube pump, the accumulated bubbles may move to the patient side during the blood return operation. It is possible to suppress the flow of the bubbles to the patient, by providing a bubble detector closer to the side of the artery side puncture needle 14 than the blood pump 13, and issuing an alarm by cutting off the blood circuit when the bubble is detected. In this case, however, the medical worker should perform the work for releasing the alarm, and the labor-saving effect by automation cannot be obtained. Further, since the blood return operation is not performed during the occurrence of the alarm, the blood is stopped in the blood circuit, and the risk of coagulation is increased. By using the tube connector 1 according to the present embodiment, it is possible to suppress the retention of bubbles, to suppress the movement of bubbles to the patient during the blood return operation, and to suppress the occurrence of an alarm when the blood return operation is performed automatically, and to suppress the interruption of the blood return operation.

Further, in this embodiment, an axial length of the communication part can be shortened as compared with a conventional one, and the tube connector 1 can be made compact. Thus, the tube connector 1 which is compact in size and can suppress the retention of bubbles can be realized.

(Evaluation of Air Bubble Discharge Performance)

Figure 8A:
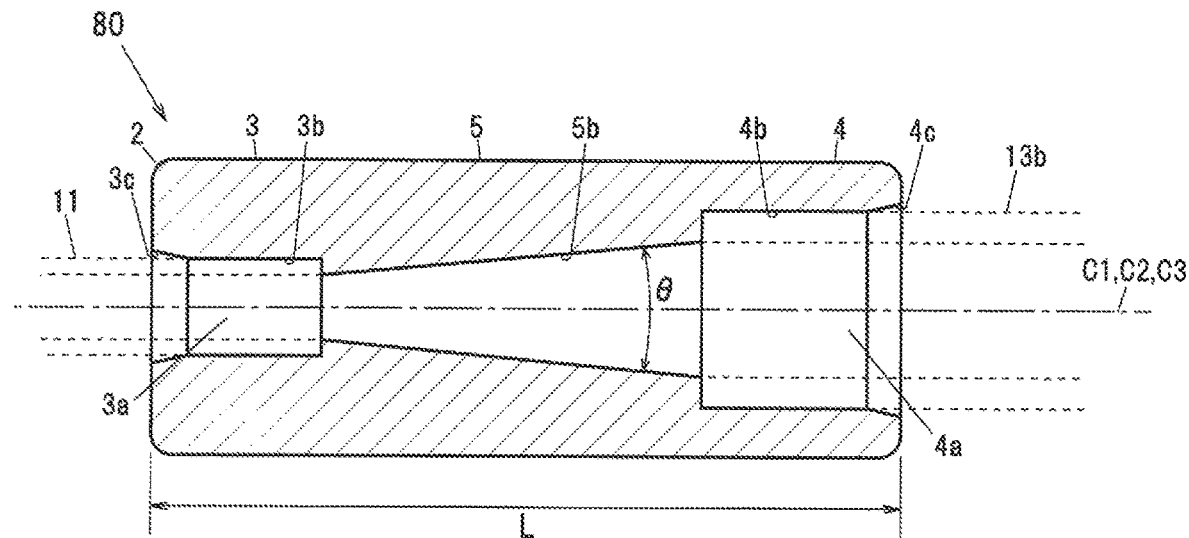
FIG. 8A is a cross-sectional view showing a tube connector in a comparative example.

A prototype of the tube connector 1 was actually prepared to evaluate the discharge performance of the bubbles. For comparison, as shown in FIG. 8A, a tube connector 80 in comparative examples, in which the central axis C1 of the first flow path 3a and the central axis C2 of the second flow path 4a are made to coincide with each other, was prepared, and the discharge performance of the bubbles was similarly evaluated. In the comparative examples, the tube connector 80 in a comparative example 1 with the spread angle (taper angle) θ in the communication flow path 5a of the communication part 5 being set to 10°, and the tube connector 80 in a comparative example 2 with the spread angle θ being set to about 65° were evaluated. The axial length L of the tube connector 80 in the comparative example 1 was 44.9 mm, and the axial length L of the tube connector 80 in the comparative example 2 was 27.0 mm. In contrast, the axial length L of the tube connector 1 according to the embodiment of the present invention was 37.0 mm. In the evaluation of the discharge performance of the bubbles, the liquid imitating the blood was made to flow from the first flow path 3a side to the second flow path 4a side of the tube connectors 1 and 80, and the flow rate (blood flow rate) was changed to measure a residual quantity of the bubbles remaining in the tube connectors 1 and 80 (suction residual air).

Figure 8B:
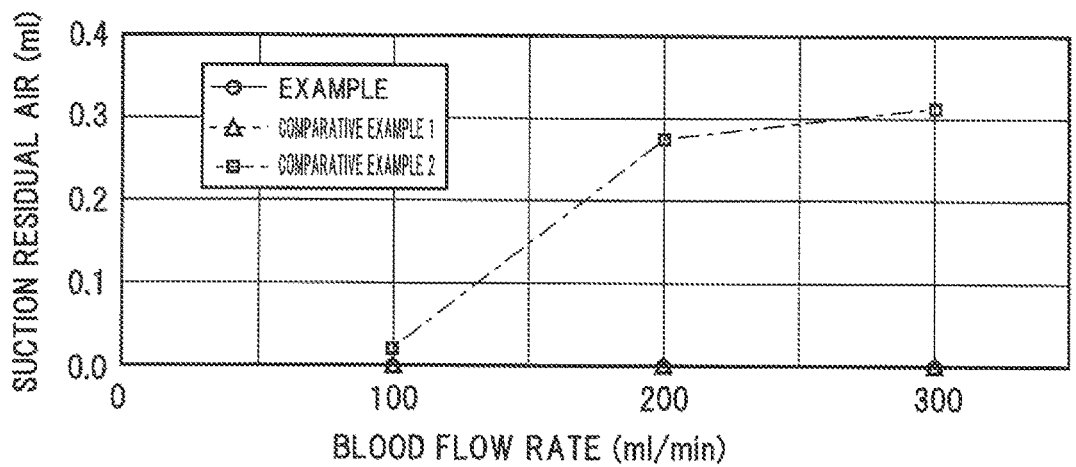
FIG. 8B is a graph showing an evaluation result of bubble discharge performance in an Example of the present invention and comparative examples.
Figure 8C:
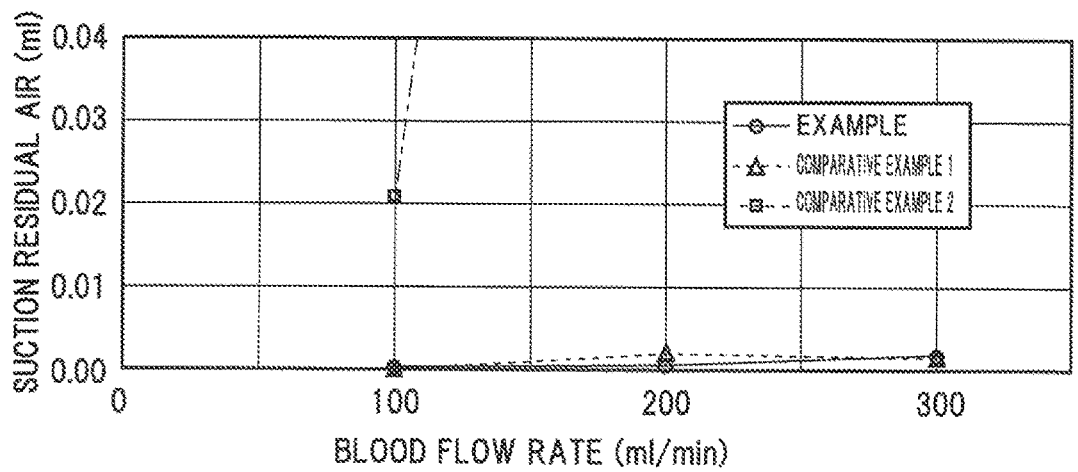
FIG. 8C is a graph showing an evaluation result of bubble discharge performance in an Example of the present invention and comparative examples.

FIGS. 8B and 8C show an evaluation result of the Example of the present invention and the comparative examples 1 and 2. It should be noted that the vertical axis of FIG. 8B is enlarged in FIG. 8C. As shown in FIGS. 8B and 8C, the tube connector 80 in the comparative example 2 in which the spread angle θ is increased to about 65°, although the axial length L can be reduced, the residual quantity of bubbles is large compared to the Example and the comparative example 1, and the retention of bubbles cannot be sufficiently suppressed.

In the Example and comparative example 1, the residual quantity of bubbles can be made very small regardless of the blood flow rate. However, the tube connector 80 in the comparative example 1 has an axial length L of 44.9 mm and a large size. For the tube connector 1 in the Example, it is confirmed that the axial length L is 37.0 mm and the size is small, and the retention of bubbles can be sufficiently suppressed.

(Summary of Embodiments)

Next, the technical concept grasped from the above-described embodiments is described with reference to sign or the like in the embodiment. However, each reference sign or the like in the following description is not limited to a member or the like specifically shown in the embodiments as constitutional elements in the scope of the claims.

[1] A tube connector (1) configured to connect between a main tube (11) comprising a flexible tubular member and a peristaltically-actuated tube (13b) comprising a flexible tubular member and being configured to be squeezed in a longitudinal direction while being compressed in a radial direction by a squeezing part (13a) to make an internal liquid flow therethrough, the tube connector (1) comprising: a first connection part (3) configured to be connected to the main tube (11); a second connection part (4) configured to be connected to the peristaltically-actuated tube (13b); a communication part (5) being provided between the first connection part (3) and the second connection part (4) and having a communication flow path (5a) for communicating between a first flow path (3a) through which fluid flows in the first connection part (3) and a second flow path (4a) through which the fluid flows in the second connection part (4); and a main body section (2) being constituted by sequentially providing the first connection part (3), the communication part (5), and the second connection part (4) in an axial direction of the main body section (2), wherein the first flow path (3a) and the second flow path (4a) are formed to have a constant diameter and are formed so as to extend along the axial direction of the main body section (2), wherein a diameter of the first flow path (3a) is smaller than a diameter of the second flow path (4a), wherein the communication flow path (5a) is formed so as to gradually enlarge in diameter from a first flow path (3a) side to a second flow path (4a) side, and wherein a central axis (C1) of the first flow path (3a) and a central axis (C2) of the second flow path (4a) are shifted toward the radial direction of the main body section (2).

[2] The tube connector (1) according to [1], wherein the central axis (C1) of the first flow path (3a) is shifted upward in use state with respect to the central axis (C2) of the second flow path (4a).

[3] The tube connector (1) according to [1] or [2], wherein an inner diameter of the main tube (11) is smaller than an inner diameter of the peristaltically-actuated tube (13b), wherein the first connection part (3) includes a first insertion hole (3b) for inserting an end part of the main tube (11) thereinto, wherein the first flow path (3a) is a hollow part of the main tube (11) inserted into the first insertion hole (3b), wherein the second connection part (4) includes a second insertion hole (4b) for inserting an end part of the peristaltically-actuated tube (13b) thereinto, and wherein the second flow path (4a) is a hollow part of the peristaltically-actuated tube (13b) inserted into the second insertion hole (4b).

[4] The tube connector (1) according to any one of [1] to [3], wherein a part of an inner peripheral surface of the first flow path (3a) and a part of an inner peripheral surface of the second flow path (4a) are provided at positions corresponding to each other in a radial direction of the main body section (2).

[5] The tube connector (1) according to any one of [1] to [3], wherein at least a part of the first flow path (3a) is disposed outside the second flow path (4a) in the radial direction of the main body section (2).

[6] An extracorporeal circulation circuit (10), comprising: a main tube (11) for extracorporeal circulation of a blood of a patient; a blood purifier (12) inserted in a middle of the main tube (11); a blood pump (13) comprising a peristaltic type pump inserted in the middle of the main tube (11) and including a peristaltically-actuated tube (13b) comprising a flexible tubular member and being configured to be squeezed in a longitudinal direction while being compressed in a radial direction by a squeezing part (13a) to make an internal liquid flow therethrough; and a pair of tube connectors (1) configured to connect both ends of the peristaltically-actuated tube (13b) to the main tube (11), wherein at least the tube connector provided on an upstream side in blood flow is the tube connector (1) according to any one of [1] to [5].

[7] The extracorporeal circulation circuit (10) according to [6], further comprising: a mounting direction regulation means for regulating a mounting direction of the tube connector (1) in such a manner that the center axis (C1) of the first flow path (3a) is shifted upward in the use state with respect to the central axis (C2) of the second flow path (4A).

[8] A blood purification device (100), comprising the extracorporeal circulation circuit (10) according to [6] or [7]; and a dialysate supply circuit (21) for supplying dialysate to the blood purifier (12).

While the embodiments of the present invention have been described, the embodiments described above are not intended to limit the invention as in the claims. It should be noted that all of the combinations of features described in the embodiments are not necessarily essential to the means for solving the problems of the invention.

The present invention can be appropriately modified and practiced without departing from the spirit of the invention. For example, although the tube connector 1 of the present invention is used for both the tube connectors on the upstream side and the downstream side of the peristaltically-actuated tube 13b, the tube connector 1 of the present invention may be used at least as the tube connector provided on the upstream side in the blood flow at the time of hemodialysis.

REFERENCE SIGNS LIST

1 Tube connector
2 Main body section
3 First connection part
3a First flow path

3b First insertion hole
4 Second connection part
4a Second flow path
4b Second insertion hole
5 Communicating part
5a Communication flow path
10 Extracorporeal circulation circuit
11 Main tube
12 Blood purifier
13 Blood pump
13a Squeezing part
13b Squeeze tube
21 Dialysis liquid supply circuit
100 Blood purification device

The invention claimed is:

1. A tube connector configured to connect between a main tube comprising a flexible tubular member and a peristaltically-actuated tube comprising a flexible tubular member and being configured to be squeezed in a longitudinal direction while being compressed in a radial direction by a squeezing part to make an internal liquid flow therethrough, the tube connector comprising:
   a first connection part configured to be connected to the main tube;
   a second connection part configured to be connected to the peristaltically-actuated tube;
   a communication part being provided between the first connection part and the second connection part and having a communication flow path for communicating between a first flow path through which fluid flows in the first connection part and a second flow path through which the fluid flows in the second connection part; and
   a main body section being constituted by sequentially providing the first connection part, the communication part, and the second connection part in an axial direction of the main body section,
   wherein the first flow path and the second flow path are formed to have a constant diameter and are formed so as to extend along the axial direction of the main body section,
   wherein a diameter of the first flow path is smaller than a diameter of the second flow path,
   wherein the communication flow path is formed so as to gradually enlarge in diameter from a first flow path side to a second flow path side, and
   wherein a central axis of the first flow path and a central axis of the second flow path are shifted toward a radial direction of the main body section.

2. The tube connector according to claim 1, wherein the central axis of the first flow path is shifted upward in use state with respect to the central axis of the second flow path.

3. The tube connector according to claim 1, wherein an inner diameter of the main tube is smaller than an inner diameter of the peristaltically-actuated tube,
   wherein the first connection part includes a first insertion hole for inserting an end part of the main tube thereinto,
   wherein the first flow path is a hollow part of the main tube inserted into the first insertion hole,
   wherein the second connection part includes a second insertion hole for inserting an end part of the peristaltically-actuated tube thereinto, and
   wherein the second flow path is a hollow part of the peristaltically-actuated tube inserted into the second insertion hole.

4. The tube connector according to claim 1, wherein a part of an inner peripheral surface of the first flow path and a part of an inner peripheral surface of the second flow path are provided at positions corresponding to each other in a radial direction of the main body section.

5. The tube connector according to claim 1, wherein at least a part of the first flow path is disposed outside the second flow path in the radial direction of the main body section.

6. An extracorporeal circulation circuit, comprising:
   a main tube for extracorporeal circulation of a blood of a patient;
   a blood purifier inserted in a middle of the main tube;
   a blood pump comprising a peristaltic type pump inserted in the middle of the main tube and including a peristaltically-actuated tube comprising a flexible tubular member and being configured to be squeezed in a longitudinal direction while being compressed in a radial direction by a squeezing part to make an internal liquid flow therethrough; and
   a pair of tube connectors configured to connect both ends of the peristaltically-actuated tube to the main tube,
   wherein at least the tube connector provided on an upstream side in blood flow is the tube connector according to claim 1.

7. The extracorporeal circulation circuit according to claim 6, further comprising:
   a mounting direction regulation unit for regulating a mounting direction of the tube connector in such a manner that the center axis of the first flow path is shifted upward in the use state with respect to the central axis of the second flow path.

8. A blood purification device, comprising the extracorporeal circulation circuit according to claim 6; and a dialysate supply circuit for supplying dialysate to the blood purifier.

* * * * *